United States Patent [19]
Armour et al.

[11] Patent Number: 5,874,060
[45] Date of Patent: Feb. 23, 1999

[54] RECOMBINANT HUMAN ANTI-LEWIS Y ANTIBODIES

[75] Inventors: Kathryn Lesley Armour, Aberdeen; Francis Joseph Carr, Balmedie, both of Great Britain; Lloyd J. Old, New York, N.Y.; Elisabeth Stockert, New York, N.Y.; Sydney Welt, New York, N.Y.; Kunio Kitamura, New York, N.Y.; Pilar Garin-Chesa, Biberach, Germany

[73] Assignee: Memorial Sloan Kettering Cancer Center, New York, N.Y.

[21] Appl. No.: 859,649

[22] Filed: May 20, 1997

Related U.S. Application Data

[62] Division of Ser. No. 207,861, Mar. 8, 1994.

[51] Int. Cl.[6] ........................ A61K 51/00; A61K 39/395
[52] U.S. Cl. ................. 424/1.49; 424/141.1; 424/152.1; 424/155.1; 424/156.1; 424/172.1; 424/174.1; 424/178.1; 424/181.1
[58] Field of Search ............................... 424/130.1, 178.1, 424/181.1, 172.1, 141.1, 138.1, 1.49, 152.1, 155.1, 156.1

[56] References Cited

U.S. PATENT DOCUMENTS 5,242,824  9/1993  Hellstrom et al. ................. 435/240.27
5,491,088  2/1996  Hellstrom et al. ................. 435/240.24

OTHER PUBLICATIONS

Queen et al (Pnas, 86:10029–10033), 1989.
Reichmann et al (Nature, 332:323–327), 1988.

*Primary Examiner*—Lila Feisee
*Assistant Examiner*—Susan Ungar
*Attorney, Agent, or Firm*—Fulbright & Jaworski, LLP.

[57] ABSTRACT

The invention provides for the production of several humanized murine antibodies specific for the antigen Lewis Y, which is recognized by the murine antibody Lewis Y. The Lewis Y antigen is expressed in normal tissues but the level of expression is higher in certain tumor types so that the antigen can be used as a marker for cells of some breast, colon, gastric, esophageal, pancreatic, duodenal, lung, bladder and renal carcinomas and gastric and islet cell neuroendocrine tumors. The invention also provides for numerous polynucleotide encoding humanized Lewis Y specific antibodies, expression vectors for producing humanized Lewis Y specific antibodies, and host cells for the recombinant production of the humanized antibodies. The invention also provides methods for detecting cancerous cells (in vitro and in vivo) using humanized Lewis Y specific antibodies. Additionally, the invention provides methods of treating cancer using humanized Lewis Y specific antibodies.

7 Claims, 4 Drawing Sheets

```
GAAGTGAAGCTGGTGGAGTCGGGGGGAGGCTTAGTGCAGCCTGGAGGGTCCCTGAAACTC
----.----+----.----+----.----+----.----+----.----+----.----+  60
CTTCACTTCGACCACCTCAGCCCCCCTCCGAATCACGTCGGACCTCCCAGGGACTTTGAG e  v  k  l  v  e  s  g  g  g  l  v  q  p  g  g  s  l  k  l

----.----+----.----+----.----+----.----+----.----+----.----+

TCCTGTGCAACCTCTGGATTCACTTTCAGT GACTATTACATGTAT TGGGTTCGCCAGACT
----.----+----.----+----.----+----.----+----.----+----.----+  120
AGGACACGTTGGAGACCTAAGTGAAAGTCA CTGATAATGTACATA ACCCAAGCGGTCTGA s  c  a  t  s  g  f  t  f  s  d  y  y  m  y  w  v  r  q  t

----.----+----.----+----.----+----.----+----.----+----.----+

CCAGAGAAGAGGCTGGAGTGGGTCGCA TACATGAGTAATGTTGGTGCTATCACCGATTAT
----.----+----.----+----.----+----.----+----.----+----.----+  180
GGTCTCTTCTCCGACCTCACCCAGCGT ATGTACTCATTACAACCACGATAGTGGCTAATA p  e  k  r  l  e  w  v  a  y  m  s  n  v  g  a  i  t  d  y

----.----+----.----+----.----+----.----+----.----+----.----+

CCAGACACTGTAAAGGGC CGATTCACCATCTCCAGAGACAATGCCAAGAGCACCCTGTAC
----.----+----.----+----.----+----.----+----.----+----.----+  240
GGTCTGTGACATTTCCCG GCTAAGTGGTAGAGGTCTCTGTTACGGTTCTCGTGGGACATG p  d  t  v  k  g  r  f  t  i  s  r  d  n  a  k  s  t  l  y

----.----+----.----+----.----+----.----+----.----+----.----+

CTGCAAATGAGCCGTCTGAGGTCTGAGGACACAGCCATGTATTACTGTGCAAGA GGGACG
----.----+----.----+----.----+----.----+----.----+----.----+  300
GACGTTTACTCGGCAGACTCCAGACTCCTGTGTCGGTACATAATGACACGTTCT CCCTGC l  q  m  s  r  l  r  s  e  d  t  a  m  y  y  c  a  r  g  t

----.----+----.----+----.----+----.----+----.----+----.----+

CGGGATGGTTCCTGGTTTGCTTAC TGGGGCCAAGGGACTCTGGTCACTGTCTCTGCA
----.----+----.----+----.----+----.----+----.----+----.--  357
GCCCTACCAAGGACCAAACGAATG ACCCCGGTTCCCTGAGACCAGTGACAGAGACGT r  d  g  s  w  f  a  y  w  g  q  g  t  l  v  t  v  s  a

```
GATGTTTTGATGACCCAAACTCCACTCTCCCTGCCTGTCAGTCTTGGAGATCAAGCCTCC
----.----+----.----+----.----+----.----+----.----+----.----+  60
CTACAAAACTACTGGGTTTGAGGTGAGAGGGACGGACAGTCAGAACCTCTAGTTCGGAGG d  v  l  m  t  q  t  p  l  s  l  p  v  s  l  g  d  q  a  s
```

```
ATCTCTTGC AGATCTAGTCAGCGCATTGTACATAGTAATGGAAACACCTATTTAGAA TGG
----.----+----.----+----.----+----.----+----.----+----.----+  120
TAGAGAACG TCTAGATCAGTCGCGTAACATGTATCATTACCTTTGTGGATAAATCTT ACC i  s  c  r  s  s  q  r  i  v  h  s  n  g  n  t  y  l  e  w
```

```
TACCTGCAGAAACCAGGCCAGTCTCCAAAGCTCCTGATCTAC AAAGTTTCCAACCGATTT
----.----+----.----+----.----+----.----+----.----+----.----+  180
ATGGACGTCTTTGGTCCGGTCAGAGGTTTCGAGGACTAGATG TTTCAAAGGTTGGCTAAA y  l  q  k  p  g  q  s  p  k  l  l  i  y  k  v  s  n  r  f
```

```
TCT GGGGTCCCAGACAGGTTCAGTGGCAGTGGATCAGGGACAGATTTCACACTCAAGATC
----.----+----.----+----.----+----.----+----.----+----.----+  240
AGA CCCCAGGGTCTGTCCAAGTCACCGTCACCTAGTCCCTGTCTAAAGTGTGAGTTCTAG s  g  v  p  d  r  f  s  g  s  g  s  g  t  d  f  t  l  k  i
```

```
AGCAGAGTGGAGGCTGAGGATCTGGGAGTTTATTACTGC TTTCAAGGTTCACATGTTCCA
----.----+----.----+----.----+----.----+----.----+----.----+  300
TCGTCTCACCTCCGACTCCTAGACCCTCAAATAATGACG AAAGTTCCAAGTGTACAAGGT s  r  v  e  a  e  d  l  g  v  y  y  c  f  q  g  s  h  v  p
```

```
TTCACG TTCGGCTCGGGGACAAAGTTGGAAATAAAA
----.+----.----+----.----+----.----+-  336
AAGTGC AAGCCGAGCCCCTGTTTCAACCTTTATTTT f  t  f  g  s  g  t  k  l  e  i  k
```

FIG. 2

```
GAGGTCCAACTGGTGGAGAGCGGTGGAGGTGTTGTGCAACCTGGCCGGTCCCTGCGCCTG
----.----+----.----+----.----+----.----+----.----+----.----+  60
CTCCAGGTTGACCACCTCTCGCCACCTCCACAACACGTTGGACCGGCCAGGGACGCGGAC e  v  q  l  v  e  s  g  g  g  v  v  q  p  g  r  s  l  r  l

----.----+----.----+----.----+----.----+----.----+----.----+

TCCTGCTCCTCGTCTGGCTTCACTTTCAGT GACTATTACATGTAT TGGGTGAGACAGGCA
----.----+----.----+----.----+----.----+----.----+----.----+ 120
AGGACGAGGAGCAGACCGAAGTGAAAGTCA CTGATAATGTACATA ACCCACTCTGTCCGT s  c  s  s  s  g  f  t  f  s  d  y  y  m  y  w  v  r  q  a

----.----+----.----+----.----+----.----+----.----+----.----+

CCTGGAAAAGGTCTTGAGTGGGTTGCA TACATGAGTAATGTTGGTGCTATCACCGACTAT
----.----+----.----+----.----+----.----+----.----+----.----+ 180
GGACCTTTTCCAGAACTCACCCAACGT ATGTACTCATTACAACCACGATAGTGGCTGATA p  g  k  g  l  e  w  v  a  y  m  s  n  v  g  a  i  t  d  y

----.----+----.----+----.----+----.----+----.----+----.----+

CCAGACACTGTGAAGGGG AGATTTACAATATCGAGAGACAACAGCAAGAACACATTGTTC
----.----+----.----+----.----+----.----+----.----+----.----+ 240
GGTCTGTGACACTTCCCC TCTAAATGTTATAGCTCTCTGTTGTCGTTCTTGTGTAACAAG p  d  t  v  k  g  r  f  t  i  s  r  d  n  s  k  n  t  l  f

----.----+----.----+----.----+----.----+----.----+----.----+

CTGCAAATGGACAGCCTGAGACCCGAAGACACCGGGGTCTATTTTTGTGCAAGA GGCACC
----.----+----.----+----.----+----.----+----.----+----.----+ 300
GACGTTTACCTGTCGGACTCTGGGCTTCTGTGGCCCCAGATAAAAACACGTTCT CCGTGG l  q  m  d  s  l  r  p  e  d  t  g  v  y  f  c  a  r  g  t

----.----+----.----+----.----+----.----+----.----+----.----+

CGTGATGGCTCGTGGTTTGCTTAC TGGGGCCAAGGGACCCCCGGTCACCGTCTCCTCA
----.----+----.----+----.----+----.----+----.----+----.---- 357
GCACTACCGAGCACCAAACGAATG ACCCCCGGTTCCCTGGGGCCAGTGGCAGAGGAGT r  d  g  s  w  f  a  y  w  g  q  g  t  p  v  t  v  s  s

```
GACATCCAGATGACCCAGAGCCCAAGCAGCCTGAGCGCCAGCGTGGGTGACAGAGTGACC
----.----+----.----+----.----+----.----+----.----+----.----+  60
CTGTAGGTCTACTGGGTCTCGGGTTCGTCGGACTCGCCGGTCGCACCCACTGTCTCACTGG d  i  q  m  t  q  s  p  s  s  l  s  a  s  v  g  d  r  v  t

----.----+----.----+----.----+----.----+----.----+----.----+
ATCACCTGT AGATCTAGTCAGCGCATTGTACATAGTAATGGAAACACCTATTTAGAA TGG
----.----+----.----+----.----+----.----+----.----+----.----+  120
TAGTGGACA TCTAGATCAGTCGCGTAACATGTATCATTACCTTTGTGGATAAATCTT ACC i  t  c  r  s  s  q  r  i  v  h  s  n  g  n  t  y  l  e  w

----.----+----.----+----.----+----.----+----.----+----.----+
TACCAGCAGACGCCAGGTAAGGCTCCAAAGCTGCTGATCTAC AAAGTTTCCAACCGATTT
----.----+----.----+----.----+----.----+----.----+----.----+  180
ATGGTCGTCTGCGGTCCATTCCGAGGTTTCGACGACTAGATG TTTCAAAGGTTGGCTAAA y  q  q  t  p  g  k  a  p  k  l  l  i  y  k  v  s  n  r  f

----.----+----.----+----.----+----.----+----.----+----.----+
TCT GGTGTGCCAAGCAGATTCAGCGGTAGCGGTAGCGGTACCGACTACACCTTCACCATC
----.----+----.----+----.----+----.----+----.----+----.----+  240
AGA CCACACGGTTCGTCTAAGTCGCCATCGCCATCGCCATGGCTGATGTGGAAGTGGTAG s  g  v  p  s  r  f  s  g  s  g  s  g  t  d  y  t  f  t  i

----.----+----.----+----.----+----.----+----.----+----.----+
AGCAGCCTCCAGCCAGAGGACATCGCCACCTACTACTGC TTTCAAGGTTCACATGTTCCC
----.----+----.----+----.----+----.----+----.----+----.----+  300
TCGTCGGAGGTCGGTCTCCTGTAGCGGTGGATGATGACG AAAGTTCCAAGTGTACAAGGG s  s  l  q  p  e  d  i  a  t  y  y  c  f  q  g  s  h  v  p

----.----+----.----+----.----+----.----+----.----+----.----+
TTCACG TTCGGCCAAGGGACCAAGCTGCAAATCACA
----.----+----.----+----.----+----.-----  336
AAGTGC AAGCCGGTTCCCTGGTTCGACGTTTAGTGT f  t  f  g  q  g  t  k  l  q  i  t

RECOMBINANT HUMAN ANTI-LEWIS Y ANTIBODIES

This application is a divisional of pending U.S. Ser. No. 08/207,861 filed Mar. 8, 1994.

FIELD OF THE INVENTION

The present invention is related to the field of molecular biology, and more particularly to humanized antibodies.

BACKGROUND

The present invention relates to the generation, by recombinant DNA methods, of novel immunoglobulins specific for the Lewis Y antigen, using, as a starting point, a murine monoclonal antibody against the same antigen.

Transformation of a normal cell to a malignant cell is often accompanied by a change in the expression of cell surface antigens. These different phenotypes can be detected using monoclonal antibodies specific for such antigens. In this way, different cancer cells can be detected and characterised (Lloyd, K. O. (1983) "Human Tumour Antigens: Detection and Characterisation with Monoclonal Antibodies" in R. B. Herberman, ed., Basic and Clinical Tumour Immunology, pp 159–214, Martinus Nijhoff, Boston). Lewis Y is a carbohydrate antigen with the structure Fucα1→2Galβ1→4[Fucα1→3]GlcNAcβ1→3R (Abe et al. (1983) J. Biol. Chem. 258 11793–11797). The Lewis Y antigen is expressed in normal tissues but the level of expression is higher in certain tumour types so that the antigen can be used as a marker for cells of some breast, colon, gastric, esophageal, pancreatic, duodenal, lung, bladder and renal carcinomas and gastric and islet cell neuroendocrine tumours. Its presence on some tumour cells is not accompanied by an increase in its serum levels, thus administered Lewis Y specific antibody is not significantly bound by soluble antigen.

Although a murine monoclonal antibody reactive against the Lewis Y antigen has potential in the imaging and treatment of certain tumours in man, this potential may be difficult to realise due to the xenogenic nature of the antibody. The problems associated with this are two-fold. First, administered xenogenic antibodies are likely to be immunogenic (Bruggemann et al (1989) J. Exp. Med. 170, 2153–2157). In this case, this would cause a human anti-mouse antibody (HAMA) response (Schroff, R. et al (1985) Cancer Res. 45, 879–885), resulting in rapid clearance of the antibody from the circulation. Second, depending upon the isotypes involved, a murine antibody may be less efficacious than a human counterpart in the stimulation of human complement or cell-mediated cytotoxicity.

To secure the advantage of a human antibody, whilst making use of the antigen-binding properties of an antibody raised in a different species, workers have made use of recombinant DNA techniques. EP120694 (Celltech) and EP125023 (Genentech) disclose the development of 'chimaeric' antibodies which comprise the variable regions of an antibody from another species and the constant regions of a human antibody. Such chimaeric antibodies have the advantage since they retain the specificity of the murine antibody but can also stimulate human Fc dependent complement fixation and cell-mediated cytotoxicity. However, the murine variable regions can still elicit a HAMA response (Bruggemann, M. et al (1989) J.Exp.Med. 170, 2153–2157) thereby limiting the value of chimaeric antibodies as diagnostic and therapeutic agents.

British Patent Application Number GB2188638A (Winter) discloses the process of humanization in which only the antigen binding-loops are transferred to a human antibody template (for example Riechmann et al., Nature, 332, 323–327; Tempest et al., (1991) Bio/Technology 9, 266–271). These loops, known as complementary-determining regions (CDRs), are mounted on a scaffold—the frameworks regions. Together these make up the variable domains. Each binding site is formed, in the most part, from three heavy chain and three light chain CDRs, although framework residues can interact with antigen, either directly or indirectly, by altering the CDR conformation. 'Reshaped' or 'humanized' antibodies made by the process of CDR-grafting retain the human constant regions necessary for the stimulation of human Fc-dependant effector functions and have less murine content than chimaeric antibodies. Consequently, humanized antibodies are less likely than chimaeric antibodies to evoke a HAMA response when administered to humans, their half-life in circulation should approach that of natural human antibodies, thereby enhancing their diagnostic and therapeutic value.

In practice, for the generation of efficacious humanized antibodies retaining the specificity of the original murine antibody, it is not usually sufficient simply to substitute CDRs. There is a requirement for the inclusion of a small number of critical murine antibody residues in the human variable region frameworks. The identity of these residues depends on the structure of both the original murine antibody and the acceptor human antibody.

The present invention provides novel humanized monoclonal antibodies specific for the Lewis Y antigen. This has been achieved by the generation of a murine monoclonal antibody reactive to the Lewis Y antigen, followed by utilisation of its variable domain structures in the design of the recombinant antibodies. Prior to the work of the inventors, it was not known that S193S or any other non-human antibody specific for the the Lewis Y antigen could be humanized so as to retain useful binding specificity.

BRIEF DESCRIPTON OF THE FIGURES

FIGS. 1 and 2 show the nucleotide and amino acid sequences of the heavy (FIG. 1) and kappa (light) chain (FIG. 2) variable regions of murine 3S193. The CDRs are boxed and residues dictated by PCR primer are underlined.

FIGS. 3 (heavy chain) and 4 (light chain) give the nucleotide sequences of the DNA fragments encoding the basic humanized variable regions and their polypeptide products. The CDRs are boxed.

SUMMARY OF THE INVENTION

One aspect of the invention is to provide humanized antibodies specific for the Lewis Y antigen.

Another aspect of the invention is to provide polynucleotides encoding humanized antibodies specific for the Lewis Y antigens. Various expression vectors comprising polynucleotides joined to promoter sequences are also provided. Similarly, another aspect of the invention is host cells transformed with expression vectors for the expression of humanized Lewis Y specific antibodies.

Another aspect of the invention is to provide humanized Lewis Y specific antibodies that are labeled with a detectable label or a therapeutic label.

Another aspect of the invention is to provide methods for treating and/or diagnosing cancer by administering a composition comprising a humanized Lewis Y specific antibody. One method of detecting cancer cells involves the steps of administering a labeled antibody (detectable label) to a patient and subsequently detecting where in the body the labeled antibody has bound.

DETAILED DESCRIPTION OF THE SPECIFIC EMBODIMENTS

As used herein, the term "humanized" antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules comprise at least one variable region (either a heavy chain of light chain variable region) and include molecules such as Fab fragments, Fab' fragments, F(ab')$_2$ fragments, Fd fragments, Fabc fragments, Fd fragments, Fabc fragments, Sc antibodies (single chain antibodies), diabodies, individual antibody light chains, individual antibody heavy chains, chimeric fusions between antibody chains and other molecules, and the like.

The term "conventional molecular biology methods" refers to techniques for manipulating polynucleotides that are well known to the person of ordinary skill in the art of molecular biology. Examples of such well known techniques can be found in *Molecular Cloning: A Laboratory Manual 2nd Edition,* Sambrook et al, Cold Spring Harbor, N.Y. (1989). Examples of conventional molecular biology techniques include, but are not limited to, in vitro ligation, restriction endonuclease digestion, PCR, cellular transformation, hybridization, electrophoresis, DNA sequencing, and the like.

The term "variable region" as used herein in reference to immunoglobulin molecules has the ordinary meaning given to the term by the person of ordinary skill in the act of immunology. Both antibody heavy chains and antibody light chains amy be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

The present invention provides humanized antibody molecules specific for Lewis Y antigen in which at least parts of the CDRs of the heavy and/or light chain variable regions of a human antibody (the receptor antibody) have been substituted by analogous parts of CDRs of a murine monoclonal antibody and the humanized antibody can specifically bind to the same as the Lewis Y antibody. In a preferred embodiment of the subject invention, the CDR regions of the humanized Lewis Y specific antibody are derived from the murine antibody 3S193. The humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitution that improve the binding properties of a humanized antibody region that is specific for the same target as the murine antibody 3S193. A minimal number of substitutions are made to the framework region in order to avoid large-scale introductions of non-human framework residues and to ensure minimal immunogenicity of the humanized antibody. The prefered donor monoclonal antibody of the present invention is the murine antibody 3S193, which is specific for the human Lewis Y cancer antigen. The humanized antibodies of the subject invention may be produced by a variety of methods useful for the production of polypeptides, e.g. in vitro synthesis, recombinant DNA production, and the like. Preferably, the humanized antibodies are produced by recombinant DNA technology. The present invention also relates to the DNA and protein sequence coding for such recombinant antibodies. The invention also provides vectors for the production of the recombinant antibodies in mammalian cell hosts.

In addition to providing for humanized Lewis Y specific antibodies, the subject invention provides for polynucleotides encoding humanized Lewis Y specific antibodies. The subject polynucleotides may have a wide variety of sequences because of the degeneracy of the genetic code. A person of ordinary skill in the art may readily change a given polynucleotide sequence encoding a humanized Lewis Y specific antibody into a different polynucleotide encoding the same humanized Lewis Y specific antibody embodiment. The polynucleotide sequence encoding the antibody may be varied to take into account factors affecting expression such as coding frequency, RNA secondary structure, and the like.

The recombinant humanized Lewis Y specific antibodies of the invention may be produced by the following process or other recombinant protein expression methods:

a. Constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine Lewis Y monoclonal antibody, and the remainder of the antibody is derived from a human immunoglobulin, thereby producing a vector for the expression of a humanized antibody heavy chain.

b. Constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine Lewis Y monoclonal antibody, and the remainder of the antibody is derived from a human immunoglobulin, thereby producing a vector for the expression of humanized antibody light chain.

c. Transferring the expression vectors to a host cell by conventional molecular biology methods to produce a transfected host cell for the expression of humanized Lewis Y specific antibodies.

d. Culturing the transfected cell by conventional molecular biology methods so as to produce humanized Lewis Y specific antibodies.

Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both.

The humanized Lewis Y specific antibodies of the invention may be produced using recombinant immunoglobulin expression technology.

The recombinant production of immunoglobulin molecules, including humanized antibodies are described in U.S. Pat. No. 4,816,397 (Boss et al), U.S. Pat. No. 4,816,567 (Cabilly et al) U.K. patent GB 2,188,638 (Winter et al), and U.K. patent GB 2,209,757. Techniques for the recombinant expression of immunoglobulins, including humanized immunoglobulins, can also be found, among other places in Goeddel et al, *Gene Expression Technology Methods in Enzymology Vol.* 185 Academic Press (1991), and Borreback, *Antibody Engineering,* W. H. Freeman (1992). Additional information concerning the generation, design and expression of recombinant antibodies can be found in Mayforth, *Designing Antibodies,* Academic Press, San Diego (1993).

The host cell used to express the recombinant antibody of the invention may be either a bacterial cell such as *Escherichia coli,* or preferably a eukaryotic cell. Preferably a mammalian cell such as a chinese hamster ovary cell, may be used. The choice of expression vector is dependent upon the choice of host cell, and may be selected so as to have the desired expression and regulatory characteristics in the selected host cell.

The general methods for construction of the vector of the invention, transfection of cells to produce the host cell of the invention, culture of cells to produce the antibody of the invention are all convnetional molecular biology methods. Likewise, once produced, the recombinant antibodies of the invention may be purified by standard procedures of the art, including cross-flow filtration, ammonium sulphate precipitation, affinity column chromatography, gel electrophoresis and the like.

The humanized antibodies of the present invention may comprise a complete antibody molecule having full length heavy and light chains, or any fragment thereof, such as the Fab or (Fab')$_2$ fragments, a heavy chain and light chain dimer, or any minimal fragment thereof such as a Fv, an SCA (single chain antibody), and the like, specific for the Lewis Y antigen molecule.

The humanized Lewis Y specific antibodies of the present invention, may be used in conjunction with, or attached to other antibodies (or parts thereof) such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g. radionucleotides may produce a detectable signal and have a therapeutic property. Examples of radionuclide labels include $^{125}$I, $^{131}$I, $^{14}$C. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The subject invention also provides for a variety of methods for treating and/or detecting cancer cells. These methods involve the administration to of humanized Lewis Y specific antibodies, either labelled or unlabelled, to a patient. One method of detecting cancer cells in a human involves the step of administering a labeled humanized Lewis Y specific antibody (labelled with a detectable label) to a human and subsequently detecting bound labeled antibody by the presence of the label.

The recombinant antibodies of this invention may also be used for the selection and/or isolation of human monoclonal antibodies, and the design and synthesis of peptide or non-peptide compounds (mimetics) which would be useful for the same diagnostic and therapeutic applications as the antibodies (e.g. Saragovi et al., (1991) *Science* 253:792–795).

When the humanized Lewis Y specific antibodies of the invention are used in vitro, the antibodies are typically administered in a composition comprising a pharmaceutical carrier. A pharmaceutical carrier can be any compatible, non-toxic substance suitable for delivery of the monoclonal antibodies to the patient, Sterile water, alcohol, fats, waxes, and inert solids may be included in the carrier. Pharmaceutically accepted adjuvants (buffering agents, dispersing agent) may also be incorporated into the pharmaceutical composition.

The humanized antibodies compositions of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science,* 15th Ed., Mack Publishing Company, Easton, Pa. (1980), which is incorporated herein by reference The subject invention provide numerous humanized antibodies specific for the Lewis Y antigen based on the discovery that the CDR regions of the murine monoclonal antibody could be spliced into a human acceptor framework so as to produce a humanized recombinant antibody specific for the Lewis Y antigen. Preferred humanized Lewis Y specific antibodies contain additional change in the framework region (or in other regions) to increasing binding for Lewis Y antigen. Particularly preferred embodiments of the invention are the exmplified humanized antibody molecules that have superior antigen binding properties.

The following examples are offered by way of illustration of the invention, and should not be interpreted as a limitation of the invention.

EXAMPLES

Unless otherwise indicated, all general recombinant DNA methodology was performed as described in "Molecular Cloning, A Laboratory Manual" (1989) Eds J. Sambrook el al., published by Cold Spring Harbour Laboratory Press, Cold Spring Harbour, N.Y. and enzymes were purchased from Life Technologies (Paisley, United Kingdom).

In the following examples these abbreviations may be employed:

dCTP deoxycytidine triphosphate dATP deoxyadenosine triphosphate dGTP deoxyguanosine triphosphate dTTP deoxythymidine triphosphate DTT dithiothreitol C cytosine A adenine G guanine T thymine PBS phosphate buffered saline PBST phosphate buffered saline containing 0.05% (v/v) TWEEN- 20™ (polyoxyethylene (20) sorbitan monolaurate)

Example 1

Isolation of the DNA sequences encoding murine 3S193 variable regions

The murine monoclonal antibody, 3S193, was produced using standard techniques following immunisation of BALB/c mice with Lewis Y-bearing tumour cells.

The variable regions sequences were determined from heavy and light chain cDNAs which were synthesised from cytoplasmic RNA, essentially as described by Tempest et al., loc cit.

1. RNA isolation

Approximately 300 μg cytoplasmic RNA was isolated from 1.5×10$^7$ 3S193-producing hybridoma cells by the method of Favalora et al., (1980) Meth Enzymol, 65, 718–749. Supernatant obtained from the culture of these cells was assayed for the presence of antibody by solid-phase ELISA using an Inno-Lia mouse monoclonal antibody isotyping kit (Innogenetics, Antwerp, Belgium). The antibody was confirmed to be IgG$_3$/k by this method.

2. cDNA synthesis

Reverse transcription of 3S193 RNA was initatiated from pirmers based on the 5' end of either the murine IgG3 (CG3FOR 5'TTAAGCTTAGACAGATGGGGCTGTTGT-TGT 3')(SEQ ID NO: 1) or the murine kappa (CK2FOR 5'GGAAGCTTGAAGATGGATACAGTTGGTGCAGC 3') (SEQ ID NO: 2) constant regions genes. The reactions consisted of 5 μg RNA, 0.5 μM CG3FOR or CK2FOR, 250 μM each dATP, dCTP, dGTP and dTTP, 50 mM Tris-HCl pH 8.3, 75 mM KCl, 10 mM DTT, 3 mM MgCl$_2$, 30 units RNase inhibitor (Pharmacia Milton Keynes, United Kingdom) in 50 μl total volume. Samples were heated at 70° C. for 10 min and then cooled at 37° C. over 30 min. 100 units M-MLV reverse transcriptase (Life Technologies, Paisley, United Kingdom) was added and the reaction allowed to proceed at 37° C. for 1 hour.

3. Amplification and cloning of VH and VK cDNA

The murine variable region cDNAs were amplifed by the PCR (Saiki et al., (1988) Science, 239, 498–491,) using variable regions primers, including those described by Orlandi et al., (1989) Proc. Natl. Acad. Sci. USA. 86, 3833–3837, and signal sequence primers, derived from those of Jones and Bendig, (1991) Bio/Technology, 9, 88–89, as well as the constant region primers which were involved in the first strand cDNA synthesis. Several primers combinations gave amplification products of the expected size. The additional primers used in the successful PCR amplifications were based on conserved regions at the 5' end of either murine VH (VH1BACK 5'AGGTSMARCTGCAG-SAGTCWGG 3')(SEQ ID NO: 3) or murine VK (VK1BACK 5'GACATTCAGCTGACCCAGTCTCCA 3') (SEQ ID NO: 4) genes or were designed from a subset of signal sequence genes of murine heavy chains (SH2BACK 5'TGGAATTCATGRACTTCDGGYTCAACTKRRTTT 3') (SEQ ID NO: 5). For PCR amplification of the VH, the reactions thus contained 5 μg RNA/cDNA hybrid, 0.5 μM CG2FOR and 0.5 μm VH1BACK or SH2BACK. For the VK, 5 μl RNA/cDNA hybrid was amplified with 0.5 μM each CK2FOR and VK1BACK. In addition, each reaction contained 250 μM each dATP, dCTP, dGTP and dTTP, 10 mM Tris-HCl pH 8.3, 50 mM KCl, 1.5 mM MgCl$_2$, 0.01% (w/v) gelatin, 0.01% (v/v) Tween 20, 0.01% v/v) NP-40 and 3 units AmpliTaq (Perkin Elmer Catus, Beaconsfield, UK). Amplification was over 25 cycles of 94° C., 30s; 50° or 550° C., 30s; 720° C., 45s plus 720° C., 5 min to end. The VH product sizes were approximately 400 bp (CG3FOR, VH1BACK) and 440 bp (VH1FOR, SH2BACK) as visualized by agarose gel electrophoresis. The VK products were of about 370 bp. The DNAs were purified on PREP-A-GENE™ (column chromatography reagent) matrix (Bio-Rad, Hemel Hempstead, UK) after excision from agarose gel.

For the VH, the CG3FOR, VH1BACK and CG2FOR, SH2BACK products were cloned into M13mpl8 and M13mpl9 (Pharmacia Milton Keynes, United Kingdom) using the restriction sites incorporated into the PCR primers and, for the CG3FOR, SH2BACK product, a Pst I site internal to the VH fragment. Clones were sequenced by the dideoxy method (Sanger et al., (1977) Proc. Natl. Acad. Sci. USA 74 5463–5467) using T7 DNA polymearse (Pharmacia, Milton Keynes, United Kingdom).

Clones were determined to contain VH inserts by comparison with known VH sequences. VH inserts corresponded to only one VH and represented both fragment orientations. The complete VH nucleotide sequence and the amino acid sequence derived by translation of the DNA sequence information are shown in FIG. 1. The extents of the CDRs, as indicated by the boxes, were determined as defined by Kabat et al., (1991) Sequences of proteins of Immunological Interest (5th edition), U.S. Department of Health and Human Services. The amino acid residue numbering system of Kabat et al., ibid, is used to indicate specific amino acid residues in both the murine and human varaible regions in this application.

For the VK, CK2FOR, VK1BACK product was similary cloned and, from the clones sequenced, two inserts were found which corresponded to an identical VK. The remaining inserts were not VK-like. Two additional amplification primers were created in order to obtain further VK clones. The framework 4 sequence of the inserts already obtained was used to design the oligonucleotide VK4FOR (5'TGGAATTCATGRACTTCDGGYTCAACTKRRTTT 3')(SEQ ID NO:6). The sequence of the 3S193 VK inserts was highly homologous to that of an VK cDNA which had previously been obtained in our laboratory and so the 5' end of this VK cDNA was used in the design of VK10BACK (5'TTGAATTCCAGTGATGJTTTGATGACCCA3') (SEQ ID No 7) as an alternative to VK1BACK. VK4FOR and VK10BACK were used in the amplification of CK2FOR-primed first strand cDNA under the conditions described above. This lead to the isolation of several inserts representing the putative 3S193 VK in both fragment orientations. The 3S193 VK nucleotide sequence and its amino acid translation are shown in FIG. 2. The CDRs are boxed. The sequence at the 3' end is the genuine 3S193 sequence as obtained from CK1FOR, VK1BACK product whereas residues at the 5' end are dictated by the VK10BACK primer and are shown underlined.

Example 2

Production of a chimaeric 3S193 antibody

The production of a chimaeric antibody, consisting of murine variable and human constant regions, is not necessary to the humanization process but can be useful as its ability to bind antigen can suggest that the correct VH and VK have been cloned from the cDNA of the hybridoma and the antibody can be used as a control in assays to assess the efficacy of the humanized antibodies.

For the first stage in its transfer to the expression vector, the VH insert from an M13 clone (example 1) was amplified using VH1FOR and VH1BACK to introduce the required restriction sites. The 50 μl reaction mixture contained approximately 100 ng M13 ssDNA, 0.5 μM each primer, 250 μM each dATP, dCTP, dGTP and dTTP, 10 mM Tris HCl pH8.3, 50 mM KCl, 1.5 mM MgCl$_2$, 0.01% (v/v) TWEEN-20™ (polyoxyethylene (20) sorbitan monolaurate) 0.01% (w/v) gelatin, 0.01% (v/v) NP-40 and 2 units THERMA-LASE™ DNA polymerase (IBI Limited, Cambridge, UK). The sample was subjected to 15 thermal cycles of 94° C., 30s; 50° C., 30s; 72° C., 1 min followed by an additional 5 min at 72° C. The product was digested with PstI and BstEII and cloned into M13VHPCR1 (Orlandi et al., loc cit).

Whilst carrying out the equivalent cloning step for the VK, the internal BglII site was deleted by the method of overlap extension (Ho et al., (1989) Gene 77, 51–59). Complementary oligonucleotides encompassing the required mutation, were each used in an amplification reaction with either VK1FOR or VK1BACK using an M13 clone of the. VK as template. The reaction mixtures contained about 100 ng M13 ssDNA, 0.5 μM each primer, 250 μm each dATP, dCTP dGTP and dTTP, 20 mM Tris HCl, pH8.8, 10 mM KCl, 10 mM (NH$_4$)$_2$SO$_4$, 2mM MgSO$_4$, 0.01% (v/v) TRITON -100™ (octoxynol) and 1 unit Vent DNA polymerase in 50μl total volume. Amplification took place over 15 cycles of 94° C., 30s; 500° C., 30s; 750° C., 1 min plus 75° C., 5 min to end. An aliquot of each product was added to a third tube containing 0.5 μM each VK1FOR and VK1BACK and the DNAs joined by overlap extension and amplified by Vent DNA polymerase under the conditions described above. The final product was digested with PvuII and BglII and cloned into the PvuII −BclI backbone of M13VKPCR1 (Orlandi et al., loc cit).

These manipulations served to place the variable regions behind promoter and signal peptide gene sequences in the correct context for expression. In the case of the VH, this resulted in some changes to the terminal residues: E1→Q, K3→Q, V5→Q, L108→T, A113→S. The genuine N-terminal residues of the VK had not been determined and so the nature of any changes introduced were unknown. There were no alterations at the C-terminus of the VK.

These expression cassettes were sequenced completely to confirm the absence of spurious mutations and were then excised from M13 RF DNA as HindIII - BamHI fragments. The VH fragment was cloned into a derivative of pSVgpt (Orlandi et al loc cit.) which contains a human IgG1 constant region gene (Takahashi et al., (1992) Cell 29, 671–679).

The VK fragment was cloned into pSVhyg (Orlandi et al., loc cit.), already containing the human kappa constant region gene (Hieter et al. (1992) Cell., 22 197–207). The vectors were cotransfected into the rat myeloma YB2/0 (Kilmartin et al. (1982) J. Cell Biol, 93, 576–582, and into the mouse myeloma Sp2/0-Ag 14 (Schulman et al., (1978) Nature 276, 269–270), both available from the American Type Culture Collection, Rockville, Md., USA as previously described (Tempest et al., loc cit). Mycophenolic acid resistant clones screened by ELISA for secretion of human IgG/kappa antibody. ELISA positive clones were expanded and antibody purified from culture medium by protein A affinity chromatography.

Example 3

Generation of humanized 3S193 antibodies

Humanized variable domains are created by transferring the antigen-binding loops of the parent antibody to human variable regions frameworks. The frameworks used in the case of 3S193 were those of KOL VH (Marquart et al., (1980) J. Mol. Biol. 141, 513–524), and REI VK (Epp et al. (1974) Eur. J. Biochem 45, 513–524).

For the basic 3S193 humanized heavy chain HuVH (FIG. 3) this involved transfer of the murine CDRs, as defined by Kabat et al, loc cit and one residue from the murine frameworks. This residue, Thr28, is part of the H1 loop discussed by Chothia and Lesk, (1987 ) J. Mol. Biol. 196, 901–917. Alternative versions of the HuVH(SEQ ID NO: 20) contained combinations of the murine residues Thr24, Ala74, Ser76 and Tyr79, with the chain being designated HuVH followed by letters corresponding to the one-letter codes of amino acid(s) included, e.g.,3S193HuVHASY (SEQ ID NO: 26). The basic 3S193 humanized kappa chain HuVK(SEQ ID NO: 25) (FIG. 4) contained only the CDRs of its murine counterpart. A variant, HuVKF(SEQ ID NO: 33), additionally included Phe71(Kabat numbering).

The 3S193 humanized variable region genes were generated from M13 phage DNAs containing a heavy or kappa variable region gene comprising the required human frameworks and irrelevant CDRs by site-directed mutagenesis. The M13 phage were grown in E.coli RZ1032 (dut⁻ ung⁻) to give single-stranded template DNA containing uracil in place of thymine. 0.5μg template DNA was mixed with 1 pmol universal M13 forward primer and 1 pmol each phosphorylated mutageneic oligonucleotides in 20 μl 40 mM Tris HCl pH7.5, 20 mM MgCl$_2$, 50 mM NaCl. The oligonucleotides were annealed to the template by heating at 80° C. for 5 min and cooling slowly at room temperature.

For the VH, the mutageneic oligonucleotides were:

CDR1 5' TACATGTAATAGTCACTGAAAGTGAAGCCAGA 3' (SEQ ID NO:18)

CDR2 5' CCCCTTCACAGTGTCTGGATAGTCGGTGATAGCACCAACA (SEQ ID NO:19)
TTACTCATGTATGCAACCCACTC 3'

CDR3 5' TTGGCCCCAGTAAGCAAACCACGAGCCATCACGGGTGCCTC (SEQ ID NO:10)
TTGCACA 3'

The template utilised for the kappa chain variable region mutagenesis actually encoded framework regions which were related but not identical to REI and the mutagenesis reaction eliminated these discrepancies (utilizing oligonucleotides not described) as well as introducing the 3S193 CDRs. The only discrepancy to be discussed specifically herein is at position 71 of the template which encoded a phenylalanine residue not present in REI sequence. This residue was retained in the 3S193 HuVKF(SEQ ID NO:33) but was changed to the REI residue in the 3S193 HuVK (SEQ ID NO: 25) in figure using the oligonucleotide REI Y71:

5' ATGGTGAAGGTGTAGTCGGTACCGC 3'(SEQ ID NO:11)

For both the HuVK(SEQ ID NO:25) and HuVKF(SEQ ID NO:33) kappa chain variable regions, the murine 3S193 CDR3 and the humanized template CDR3 were identical, so alteration of CDR3 was not required. Limited differences between the mouse and humanized template CDRs 1 and 2 did require alteration of the humanized template CDRs 1 and 2 and the mutagenizing oligonucleotides utilised were:

(SEQ ID NO:12)
CDR1 5' ATTCTAAATAGGTGTTTCCATTACTATGTACAATGCGC
TGACTAGATCT3'

CDR2 5' ACCAGAAAATCGGTTGGAAACTTTGT 3' (SEQ ID NO:13)

Once the oligonucleotides had been annealed to the template, dATP, dCTP, dGTP and dTTP were added to 250 µM final concentration, DTT to 7 mM, ATP to 1 mM with 0.5 units T7 DNA polymearse (United States Biochemical, Cleveland, Ohio, USA) and 0.5 units T4 DNA ligase (Life Technologies, Paisley, UK) in the same buffer. The 30 µl reaction was incubated at room temperature, 1 h and the DNA ethanol precipitated. In order to nick the parental strand, the DNA was dissolved in 50 µl 60 mM Tris HCl pH8.0, 1 mM EDTA, 1 mM DTT, 0.1 mg/ml BSA containing 1 unit uracil DNA glycosylase (Boehringer Mannheim, Lewis, Sussex, UK) and incubated 37° C., 1 h before NaOH was added to 0.2M and incubation continued at room temperature for 5 min. The DNA was ethanol precipitated, dissolved in 20 µl TE and the insert fragment amplified by PCR. The reaction mixture contained 2 µl mutant DNA, 0.5 µM each M13 forward and reverse primers, 250 µM each of dATP, dCTP, dGTP and dTTP, 10 mM Tris HCl pH8.3, 50 mM KCl, 1.5 mM MgCl$_2$, 0.01% TWEEN-20™ (polyoxyethylene (20) sorbitan monolaurate), 0.01% gelatin, 0.01% NP-40 and 2 units THERMALASE™ (IBI, Cambridge, UK) in 50 µl. Amplification was achieved with 15 cycles of 94° C., 30s; 50° C., 30s; 72° C., 1 min; ending with 72° C., 5 min. The product DNAs were cloned into M13mp19 as HindIII-BamHI fragments. Representative clones were sequenced. The HindIII - BamHI fragments were excised from RF DNA of accurately-mutated clones and transferred to the pSVgpt and pSVhyg expression vectors as described in Example 2.

Additional mutagenesis to the 3S193 HuVH (SEQ ID NO: 20), to introduce the murine residues Thr24 and Ala74+/- Ser 76+/- Tyr79, was carried out by overlap extension (Ho et al., loc cit; see example 2) using the M13-based humanized variable region gene, 3S193HuVH(SEQ ID NO:20), as template. Two complementary oligonucleotides encompassing the mutations were each used in an amplification reaction with the appropriate universal pUC/M13 primer. The mutagenic oligonucleotides were:

For Thr24 (coding strand)

5' CTGTCCTGCTCCACGTCTGGCTTCA 3' (SEQ ID NO:14)

(complementary strand) 5' TGAAGCCAGACGTGGAGCAGGACAG 3' (SEQ ID NO:15)

For Ala74 Ser76 Tyr79 (coding strand)
5' TCGAGAGACAACGCCAAGAGCACATTG-TACCTGCAAATGGA 3'(SEQ ID NO:16)

For Ala 74 +/- Ser76 (complementary strand).
5' TCCATTTGCAGGAACAATGTG(T/C)TCTTGGC GTTGTCTCTCGA 3'(SEQ ID NO:17)

The initial pair of reaction mixtures contained ~100 ng single-stranded M13 DNA, 0.5 µM mutagenic primer, 0.5 µM universal pUC/M13 primer and these, and the subsequent joining reactions, were carried out using Vent DNA polymearse as described in Example 2. The HindIII - BamHI fragments were cloned, sequenced and re-cloned for expression as already described.

The transfection of myeloma cells and their selection and expansion was carried out as Example 3. As well as transfections to give humanized antibodies (such HuVH(SEQ ID NO:20)/HuVK(SEQ ID NO:25) and HuVH(SEQ ID NO:20) /HuVKF(SEQ ID NO:33), chimaeric and humanized antibody chain expression vectors were co-transfected to give mixed antibodies which would allow the efficacy of the humanized chains to be examined individually. The HuVHT (SEQ ID NO:21), HuVHA(SEQ ID NO:21), HuVHAS(SEQ ID NO:23), and HuVHASY(SEQ ID NO:24) DNAs were transfected with the HuVHF vector.

Example 4

Assessment of properties of humanized antibodies

The recombinant antibodies were tested by several methods.

ELISAs against synthetic antigens

Terasaki plates were coated with 10 µl/well synthetic antigen (as shown in table 1, purchased from Chembiomed, Edmonton, Canada or BioCarb AB Lund, Sweden) at 1 µg/ml in water by drying overnight at room temperature. The plates were blocked for 1 hour at room temperature using PBS/3% BSA and washed three times with PBS. Serial dilutions of test antibodies in PBS/3% BSA were applied to the wells and the plates incubated for 1 hour before washing as above. Suitable anti-murine antibody or anti-human antibody alkaline phosphatase-conjugated antibodies were diluted in PBS/3% BSA and incubated in the wells for 1.5 h. After washing, colour was developed using diethanolamine and p-nitrophenyl phosphate at 37° C. for about 20 min and the absorbances measured at 405 mn.

The performances of the antibodies in these ELISAs are illustrated by table 1 which gives the minimum of concentrations of the test antibodies required to give a signal above background. It can be seen that all of the recombinant antibodies are able to bind to the Lewis Y antigen and have varying amounts of reactivity towards the related antigens shown here. Some antibodies, for example HuVH(SEQ ID NO:20)/HuVK(SEQ ID NO:25) and HuVHT/HuVKF HuVHT (SEQ ID NO:21)/HuVKF(SEQ ID NO:33), retain the specificity of the murine 3S193.

Serological-assays against-native Lewis Y antigen

Recombinant antibodies were tested in mixed hemadsorption resetting assays (Rettig et al. (1987) J. Immunol 138, 4484–4489; Rettig et al., (1985) Cancer Res. 45. 815–821) for their ability to bind to MCF-7 target cells (human breast line) and to negative control Effron melanoma cells. The cells were grown in 60-well Terasaki plates to form confluent monolayers. Cells were washed twice with PBS/0.5% BSA and 10 µl of antibody added to the cells (antibodies serially diluted in DMEM without foetal calf serum). Incubation with test antibody was continued at room temperature for 1 hour after which cells were washed three times with PBS/0.5% BSA and incubated with human red blood cells (type 0 +) conjugated to protein A (Pierce, Illinois, USA) diluted in PBS/0.5% BSA. Incubation with the indicator cells was continued at room temperature for 30 min after which unbound protein A-red blood cells were removed by washing twice with PBS/0.5% BSA. The percentage rosetting for each dilution of antibody was determined and the minimum concentration of antibody giving 50% or greater resetting calculated. None of the antibodies showed a reaction to the negative –control lines. The 50% resetting values for the MCF-7 cells are given in table 2.

In order to measure cytotoxicity against MCF-7 cells, the cells were plated at approximately 100 cells/well in medium and grown overnight. The wells were emptied and dilution of test antibody added in medium. The plates were incubated 37° C., 5% $CO_2$, for 45min and then 10 µl human serum/medium (1:3) added to each well. After 4 h the plates were rinsed twice with absolute methanol, fixed with methanol for 10 min, rinsed in distilled water, stained with 2% Giemsa stain in PBS for 25 min, and rinsed again in distilled water.

Plates were analyzed under the light microscope and the percent cytotoxicity of a given antibody dilution was calculated as follows:

(1 - No of cells in well treated with antibody & complement)×100 (%)
  No of cells in well treated with culture medium only The minimum concentration of antibody giving 50% or greater lysis is shown in table 3. No cytotoxicity was observed when Effron cells were used as the target.

These results support those of the ELISAs against the synthetic Lewis Y antigen by showing that the recombinant antibodies are able to bind to natural $Le^y$ determinants on the cell surface. Some of the decrepancy is performance between the most effective humanized antibodies (for example HuVHT(SEQ ID NO: 21)/HuVKF(SEQ ID NO: 33) and HuVHASY(SEQ ID NO: 24)/HuVKF(SEQ ID NO: 33)) and murine 3S193, which varied according to the assay employed, might be explained by the ability of murine $IgG_3$ antibodies (such as 3S193) to participate in co-operative binding to antigen (Greenspan and Cooper (1992) Immunology Today 13, 164–168).

Some of the recombinant antibodies showed cross-reactivity to Lewis Y-related antigens. To see whether this would cause hemolysis, the antibodies were incubated with $^{51}Cr$-labeled erythrocytes in the presence of human serum (Nayayarna et al. (1978) Proc. Natl. Acad. Sci. USA 7G 3486). None of the recombinant antibodies caused cell lysis detectable above a background for cells incubated with PBS alone. This suggests that the cross-reactivity of therapeutically or diagnostically administered antibody would not itself cause a problem although it would be preferable to use an antibody specific for the Lewis-Y antigen to ensure that the maximum amount of antibody is available for binding to the target cells.

These results demonstrate the suitability of antibodies such as 3S193 HuVH(SEQ ID NO: 20)/HuVK(SEQ ID NO: 25) or 3S193 HuVHT(SEQ ID NO: 21)/HuVKF(SEQ ID NO: 33) for used in the diagnosis and treatment of Lewis Y—bearing cancers.

Table 4 provides the amino acid sequences of the varaible regions of the the 3S193 heavy and light chains. Additionally, Table 4 provides the amino acid sequences of the variable regions of several humanized antibody chains derived from 3S193.

TABLE 1

ELISAs against synthetic Lewis Y and related antigens

| Antigen<br>Antibody | Le'-HSA | Le'-KLH | Le' | Htype2 | Y– | Le' | Le' | Htype1 | HSA |
| --- | --- | --- | --- | --- | --- | --- | --- | --- | --- |
| Experiment A | | | | | | | | | |
| murine | 0.10 | 0.025 | 100 | +/– | –/+ | – | –/+ | –/+ | – |
| MuVH (SEQ ID NO: 18/<br>MuVKF (SEQ ID NO: 19<br>with the proviso that amino acid 71 is not Gly but Phe) | 0.10 | 0.10 | 100 | 50 | – | – | – | – | – |
| MuVH (SEQ ID NO: 18)/HuVK (SEQ ID NO: 25) | 0.025 | 0.025 | 25 | 6.25 | 100 | +/– | +/– | 100 | +/– |
| MuVH (SEQ ID NO: 18)/HuVK (SEQ ID NO: 25) | 0.025 | 0.05 | 6.25 | 1.56 | 50 | 100 | 50 | 25 | 100 |
| HuVH (SEQ ID NO: 20)/HuVK (SEQ ID NO: 25) | 0.39 | 0.39 | +/– | –/+ | –/+ | – | +/– | –/+ | – |
| HuVH (SEQ ID NO: 20)/HuVK (SEQ ID NO: 33) | 0.39 | 0.39 | 50 | 50 | 100 | +/– | +/– | +/– | –/+ |
| HuVHT (SEQ ID NO: 21)/HuVK (SEQ ID NO: 25) | 0.39 | 0.39 | +/– | 25 | +/– | +/– | +/– | 100 | –/+ |
| HuVHT (SEQ ID NO: 21)/HuVKF (SEQ ID NO: 33) | 0.10 | 0.39 | +/– | +/– | –/+ | –/+ | –/+ | –/+ | –/+ |
| Experiment B | | | | | | | | | |
| MuVH (SEQ ID NO: 18)/HuVK (SEQ ID NO: 25) | 0.025 | 0.025 | 25 | 6.25 | +/– | +/– | +/– | +/– | – |
| HuVHT (SEQ ID NO: 21)/HuVKF (SEQ ID NO: 33) | 0.10 | 0.10 | +/– | +/– | – | – | – | – | – |
| HuVHA (SEQ ID NO: 22)/HuVKF (SEQ ID NO: 25) | 0.10 | 0.10 | +/– | +/– | – | – | – | – | – |

TABLE 1-continued

ELISAs against synthetic Lewis Y and related antigens

| Antigen<br>Antibody | Le'-HSA | Le'-KLH | Le' | Htype2 | Y- | Le' | Le' | Htype1 | HSA |
|---|---|---|---|---|---|---|---|---|---|
| HuVHAS (SEQ ID NO: 23)/HuVKF (SEQ ID NO: 33) | 0.10 | 0.10 | +/- | +/- | - | - | - | - | - |
| HuVHASY (SEQ ID NO: 24)/HuVKF (SEQ ID NO: 33) | 0.10 | 0.10 | 100 | +/- | +/- | - | - | - | - |

Values are minimum antibody concentrations (μg/ml) which show positive. -, negative, -/+, trace; +/-, weakly positive at highest concentration tested (100 μg/ml).

TABLE 2

ROSETTING ASSAY

| Antibody | Experiment A | Experiment B |
|---|---|---|
| murine | 0.0016 | n.t. |
| MuVH(SEQ ID NO:18)/MuVK(SEQ ID NO:19) | 0.0031 | n.t. |
| MuVH(SEQ ID NO:18)/HuVK(SEQ ID NO:25) | 0.0016 | 0.0031 |
| MuVH(SEQ ID NO:18)/HuVKF(SEQ ID NO:33) | 0.0031 | n.t. |
| HuVH(SEQ ID NO:18)/HuVKF(SEQ ID NO:33) | 0.0063 | n.t. |
| HuVH(SEQ ID NO:20)/HuVK(SEQ ID NO:25) | 0.0063 | n.t. |
| HuVH(SEQ ID NO:20)/HuVKF(SEQ ID NO:33) | 0.0125 | n.t. |
| HuVHT(SEQ ID NO:21)/HuVK(SEQ ID NO:25) | 0.0063 | 0.0125 |
| HuVKT(SEQ ID NO:21)/Hu/VKF(SEQ ID NO:33) | n.t. | 0.0125 |
| HuVHA(SEQ ID NO:22)/HuVKF(SEQ ID NO:33) | n.t. | 0.0125 |
| HuVHAS(SEQ ID NO:23)/HuVKF(SEQ ID NO:33) | n.t. | 0.063 |

Valves are the minimum antibody concentrations (μg/ml) which show at least 50% rosetting using MCF-7 as the target cell line.

TABLE 3

CYTOTOXICITY ASSAY

| Antibody | Experiment A | Experiment B |
|---|---|---|
| murine | 0.10 | n.t. |
| MuVH(SEQ ID NO:18)/MuVK(SEQ ID NO:19) | 0.39 | n.t. |
| MuVH(SEQ ID NO:18)/HuVK(SEQ ID NO:25) | 0.39 | 0.39 |
| MuVH(SEQ ID NO:18)/HuVKF(SEQ ID NO:33) | 0.20 | n.t. |
| HuVH(SEQ ID NO:20)/HuVK(SEQ ID NO:25) | 3.13 | n.t. |
| HuVH(SEQ ID NO:20)/HuVKF(SEQ ID NO:33) | 1.56 | n.t. |
| HuVHT(SEQ ID NO:21)/HuVK(SEQ ID NO:25) | 1.56 | n.t. |
| HuVHT(SEQ ID NO:21)/HuVKF(DEQ ID NO:33) | 0.78 | 1.56 |
| HuVHA(SEQ ID NO:22)/HuVKF(SEQ ID NO:33) | n.t. | 6.25 |
| HuVHAS(SEQ ID NO:23)/HuVKF(SEQ ID NO:33) | n.t. | 3.13 |
| HuVHASY (SEQ ID NO:24)/HuVKF(SEQ ID NO:33) | n.t. | 1.56 |

Valves are the minimum antibody concentrations (μg/ml) which show at least 50% rosetting using MCF-7 as the target cell line.

TABLE 4

3S193 Murine Heavy Chain Variable Region--
3S193 MuVH

EVKLVESGGGLVQPGGSLKLSCATSGFTFSDYYMYWVRQTPEKR
LEWVAYMSNVGAITDYPDTVKGRFTISRDNAKSTLYLQMSRLRS
EDTAMYYCARGTRDGSWFAYWGQGTLVTVSA (SEQ ID NO:18)
3S193 Murine Light Chain Variable Region--
3S193 MuVK DVLMTQTPLSLPVSLGDQASISCRSSQRIVHSNGNTYLEWYLQK
PGQSPKLLIYKVSNRFSGVPDRFSGSGSGTDFTLKISRVEAEDL
GVYYCFQGSHVPFTFGSGTKLEIK (SEQ ID NO:19)
Humanized 3S193 Heavy Chain Variable Region--
3S193 HuVH EVQLVESGGGVVQPGRSLRLSCSSSGFTFSDYYMYWVRQAPGKG
LEWVAYMSNVGAITDYPDTVKGRFTISRDNSKNTLFLOMDSLRP
EDTGVYFCARGTRDGSWFAYWGQGTPVTVSS (SEQ ID:20)
Humanized 3S193 Heavy Chain Variable Region--
3S193 HuVHT EVQLVESGGGVVQPGRSLRLSCSTSGFTFSDYYMYWVRQAPGKG
LEWVAYMSNVGAITDYPDTVKGRFTISRDNSKNTLFLQMDSLRP
EDTGVYFCARGTRDGSWFAYWGQGTPVTVSS (SEQ ID NO:21)
Humanized 3S193 Heavy Chain Variable Region--
3S193HuVHA EVQLVESGGGVVQPGRSLRLSCSSSGFTFSDYYMYWVRQAPGKG
LEWVAYMSNVGAITDYPDTVKGRFTISRDNAKNTLFLQMDSLRP
EDTGVYFCARGTRDGSWFAYWGQGTPVTVSS (SEQ ID NO:22)
Humanized 3S193 Heavy Chain Variable Region--
3S193HuVHAS EVQLVESGGGVVQPGRSLRLSCSSSGFTFSDYYMYWVRQAPGKG
LEWVAYMSNVGAITDYPDTVKGRFTISRDNAKSTLFLQMDSLRP
EDTGVYFCARGTRDGSWFAYWGQGTPVTVSS (SEQ ID NO:23)
Humanized 3S193 Heavy Chain Variable Region--
3S193HuVHASY EVQLVESGGGVVQPGRSLRLSCSSSGFTFSDYYMYWVRQAPGKG
LEWVAYMSNVGAITDYPDTVKGRFTISRDNAKSTLYLQMDSLRP
EDTGVYFCARGTRDGSWFAYWGQGTPVTVSS (SEQ ID NO:24)
Humanized 3S193 Light Chain Variable Region--
3S193HuVK DIQMTQSPSSLSASVGDRVTITCRSSQRIVHSNGNTYLEWYQQT
PGKAPKLLIYKVSNRFSGVPSRFSGSGSGTDYTFTISSLQPEDI
ATYYCFQGSHVPFTFGQGTKLQIT (SEQ ID NO:25)

Incorporation by reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:1:

TTAAGCTTAG ACAGATGGGG CTGTTGTTGT　　　　　　　　　　30

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:2:

GGAAGCTTGA AGATGGATAC AGTTGGTGCA GC　　　　　　　　32

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:3:

AGGTSMARCT GCAGSAGTCW GG　　　　　　　　　　　　22

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:4:

GACATTCAGC TGACCCAGTC TCCA　　　　　　　　　　　24

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:5:

TGGAATTCAT GRACTTCDGG YTCAACTKRR TTT 33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:6:

TGGAATTCAT GRACTTCDGG YTCAACTKRR TTT 33

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:7:

TTGAATTCCA GTGATGTTTT GATGACCCA 29

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:8:

TACATGTAAT AGTCACTGAA AGTGAAGCCA GA 32

(2) INFORMATION FOR SEQ ID NO:9:

(i) SEQUENCE CHARACTERISTICS:
        (A) LENGTH: 63 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:9:

CCCCTTCACA GTGTCTGGAT AGTCGGTGAT AGCACCAACA TTACTCATGT ATGCAACCCA 60

CTC 63

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:10:

TTGGCCCCAG TAAGCAAACC ACGAGCCATC ACGGGTGCCT CTTGCACA 48

( 2 ) INFORMATION FOR SEQ ID NO:11:

( i ) SEQUENCE CHARACTERISTICS:
　　　　　　　　( A ) LENGTH: 25 base pairs
　　　　　　　　( B ) TYPE: nucleic acid
　　　　　　　　( C ) STRANDEDNESS: unknown
　　　　　　　　( D ) TOPOLOGY: unknown ( i i ) MOLECULE TYPE: DNA ( x i ) SEQUENCE DESCRIPTION: SEQ ID NO:11:

ATGGTGAAGG TGTAGTCGGT ACCGC　　　　　　　　　　　　　　　　　　　　　25

( 2 ) INFORMATION FOR SEQ ID NO:12:

( i ) SEQUENCE CHARACTERISTICS:
　　　　　　　　( A ) LENGTH: 49 base pairs
　　　　　　　　( B ) TYPE: nucleic acid
　　　　　　　　( C ) STRANDEDNESS: unknown
　　　　　　　　( D ) TOPOLOGY: unknown ( i i ) MOLECULE TYPE: DNA ( x i ) SEQUENCE DESCRIPTION: SEQ ID NO:12:

ATTCTAAATA GGTGTTTCCA TTACTATGTA CAATGCGCTG ACTAGATCT　　　　　　　　　49

( 2 ) INFORMATION FOR SEQ ID NO:13:

( i ) SEQUENCE CHARACTERISTICS:
　　　　　　　　( A ) LENGTH: 26 base pairs
　　　　　　　　( B ) TYPE: nucleic acid
　　　　　　　　( C ) STRANDEDNESS: unknown
　　　　　　　　( D ) TOPOLOGY: unknown ( i i ) MOLECULE TYPE: DNA ( x i ) SEQUENCE DESCRIPTION: SEQ ID NO:13:

ACCAGAAAAT CGGTTGGAAA CTTTGT　　　　　　　　　　　　　　　　　　　　26

( 2 ) INFORMATION FOR SEQ ID NO:14:

( i ) SEQUENCE CHARACTERISTICS:
　　　　　　　　( A ) LENGTH: 25 base pairs
　　　　　　　　( B ) TYPE: nucleic acid
　　　　　　　　( C ) STRANDEDNESS: unknown
　　　　　　　　( D ) TOPOLOGY: unknown ( i i ) MOLECULE TYPE: DNA ( x i ) SEQUENCE DESCRIPTION: SEQ ID NO:14:

CTGTCCTGCT CCACGTCTGG CTTCA　　　　　　　　　　　　　　　　　　　　　25

( 2 ) INFORMATION FOR SEQ ID NO:15:

( i ) SEQUENCE CHARACTERISTICS:
　　　　　　　　( A ) LENGTH: 25 base pairs
　　　　　　　　( B ) TYPE: nucleic acid
　　　　　　　　( C ) STRANDEDNESS: unknown
　　　　　　　　( D ) TOPOLOGY: unknown ( i i ) MOLECULE TYPE: DNA ( x i ) SEQUENCE DESCRIPTION: SEQ ID NO:15:

TGAAGCCAGA CGTGGAGCAG GACAG　　　　　　　　　　　　　　　　　　　　　25

( 2 ) INFORMATION FOR SEQ ID NO:16:

( i ) SEQUENCE CHARACTERISTICS:
　　　　　　　　( A ) LENGTH: 41 base pairs
　　　　　　　　( B ) TYPE: nucleic acid (C) STRANDEDNESS: unknown
(D) TOPOLOGY: unknown (ii) MOLECULE TYPE: DNA (xi) SEQUENCE DESCRIPTION: SEQ ID NO:16:

TCGAGAGACA ACGCCAAGAG CACATTGTAC CTGCAAATGG A        41

(2) INFORMATION FOR SEQ ID NO:17:

(i) SEQUENCE CHARACTERISTICS:
(A) LENGTH: 41 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:17:

TCCATTTGCA GGAACAATGT GYTCTTGGCG TTGTCTCTCG A        41

(2) INFORMATION FOR SEQ ID NO:18:

(i) SEQUENCE CHARACTERISTICS:
(A) LENGTH: 119 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:18:

| Glu | Val | Lys | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Thr | Ser | Gly | Phe | Thr | Phe | Ser | Asp | Tyr |
|---|---|---|---|---|---|---|---|---|---|---|---|---|---|---|---|
| | | | 20 | | | | 25 | | | | | 30 | | | |

| Tyr | Met | Tyr | Trp | Val | Arg | Gln | Thr | Pro | Glu | Lys | Arg | Leu | Glu | Trp | Val |
|---|---|---|---|---|---|---|---|---|---|---|---|---|---|---|---|
| | | 35 | | | | | 40 | | | | | 45 | | | |

| Ala | Tyr | Met | Ser | Asn | Val | Gly | Ala | Ile | Thr | Asp | Tyr | Pro | Asp | Thr | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ala | Lys | Ser | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Ser | Arg | Leu | Arg | Ser | Glu | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Thr | Arg | Asp | Gly | Ser | Trp | Phe | Ala | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ala |
|---|---|---|---|---|---|---|
| | | 115 | | | | |

(2) INFORMATION FOR SEQ ID NO:19:

(i) SEQUENCE CHARACTERISTICS:
(A) LENGTH: 112 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:19:

| Asp | Val | Leu | Met | Thr | Gln | Thr | Pro | Leu | Ser | Leu | Pro | Val | Ser | Leu | Gly |
|---|---|---|---|---|---|---|---|---|---|---|---|---|---|---|---|
| 1 | | | | 5 | | | | | 10 | | | | | 15 | |

| Asp | Gln | Ala | Ser | Ile | Ser | Cys | Arg | Ser | Ser | Gln | Arg | Ile | Val | His | Ser |
|---|---|---|---|---|---|---|---|---|---|---|---|---|---|---|---|
| | | | 20 | | | | 25 | | | | | 30 | | | |

```
Asn Gly Asn Thr Tyr Leu Glu Trp Tyr Leu Gln Lys Pro Gly Gln Ser
         35                  40                 45

Pro Lys Leu Leu Ile Tyr Lys Val Ser Asn Arg Phe Ser Gly Val Pro
     50              55                  60

Asp Arg Phe Ser Gly Ser Gly Ser Gly Thr Asp Phe Thr Leu Lys Ile
 65              70                  75                      80

Ser Arg Val Glu Ala Glu Asp Leu Gly Val Tyr Tyr Cys Phe Gln Gly
                 85              90                      95

Ser His Val Pro Phe Thr Phe Gly Ser Gly Thr Lys Leu Glu Ile Lys
             100             105                 110
```

(2) INFORMATION FOR SEQ ID NO:20:

(i) SEQUENCE CHARACTERISTICS:
        (A) LENGTH: 119 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:20:

```
Glu Val Gln Leu Val Glu Ser Gly Gly Gly Val Val Gln Pro Gly Arg
 1               5                  10                  15

Ser Leu Arg Leu Ser Cys Ser Ser Ser Gly Phe Thr Phe Ser Asp Tyr
             20                  25                  30

Tyr Met Tyr Trp Val Arg Gln Ala Pro Gly Lys Gly Leu Glu Trp Val
         35                  40                  45

Ala Tyr Met Ser Asn Val Gly Ala Ile Thr Asp Tyr Pro Asp Thr Val
     50                  55                  60

Lys Gly Arg Phe Thr Ile Ser Arg Asp Asn Ser Lys Asn Thr Leu Phe
 65              70                  75                      80

Leu Gln Met Asp Ser Leu Arg Pro Glu Asp Thr Gly Val Tyr Phe Cys
                 85                  90                  95

Ala Arg Gly Thr Arg Asp Gly Ser Trp Phe Ala Tyr Trp Gly Gln Gly
             100                 105                 110

Thr Pro Val Thr Val Ser Ser
             115
```

(2) INFORMATION FOR SEQ ID NO:21:

(i) SEQUENCE CHARACTERISTICS:
        (A) LENGTH: 119 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:21:

```
Glu Val Gln Leu Val Glu Ser Gly Gly Gly Val Val Gln Pro Gly Arg
 1               5                  10                  15

Ser Leu Arg Leu Ser Cys Ser Thr Ser Gly Phe Thr Phe Ser Asp Tyr
             20                  25                  30

Tyr Met Tyr Trp Val Arg Gln Ala Pro Gly Lys Gly Leu Glu Trp Val
         35                  40                  45

Ala Tyr Met Ser Asn Val Gly Ala Ile Thr Asp Tyr Pro Asp Thr Val
     50                  55                  60

Lys Gly Arg Phe Thr Ile Ser Arg Asp Asn Ser Lys Asn Thr Leu Phe
 65              70                  75                      80
```

```
            Leu  Gln  Met  Asp  Ser  Leu  Arg  Pro  Glu  Asp  Thr  Gly  Val  Tyr  Phe  Cys
                           85                       90                       95

Ala  Arg  Gly  Thr  Arg  Asp  Gly  Ser  Trp  Phe  Ala  Tyr  Trp  Gly  Gln  Gly
                          100                      105                      110

Thr  Pro  Val  Thr  Val  Ser  Ser
                          115
```

( 2 ) INFORMATION FOR SEQ ID NO:22:

( i ) SEQUENCE CHARACTERISTICS:
        ( A ) LENGTH: 119 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:22:

```
            Glu  Val  Gln  Leu  Val  Glu  Ser  Gly  Gly  Gly  Val  Val  Gln  Pro  Gly  Arg
            1                    5                        10                       15

Ser  Leu  Arg  Leu  Ser  Cys  Ser  Ser  Ser  Gly  Phe  Thr  Phe  Ser  Asp  Tyr
                           20                       25                       30

Tyr  Met  Tyr  Trp  Val  Arg  Gln  Ala  Pro  Gly  Lys  Gly  Leu  Glu  Trp  Val
                           35                       40                       45

Ala  Tyr  Met  Ser  Asn  Val  Gly  Ala  Ile  Thr  Asp  Tyr  Pro  Asp  Thr  Val
                     50                        55                       60

Lys  Gly  Arg  Phe  Thr  Ile  Ser  Arg  Asp  Asn  Ala  Lys  Asn  Thr  Leu  Phe
            65                            70                       75                   80

Leu  Gln  Met  Asp  Ser  Leu  Arg  Pro  Glu  Asp  Thr  Gly  Val  Tyr  Phe  Cys
                           85                       90                       95

Ala  Arg  Gly  Thr  Arg  Asp  Gly  Ser  Trp  Phe  Ala  Tyr  Trp  Gly  Gln  Gly
                          100                      105                      110

Thr  Pro  Val  Thr  Val  Ser  Ser
                          115
```

( 2 ) INFORMATION FOR SEQ ID NO:23:

( i ) SEQUENCE CHARACTERISTICS:
        ( A ) LENGTH: 119 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:23:

```
            Glu  Val  Gln  Leu  Val  Glu  Ser  Gly  Gly  Gly  Val  Val  Gln  Pro  Gly  Arg
            1                    5                        10                       15

Ser  Leu  Arg  Leu  Ser  Cys  Ser  Ser  Ser  Gly  Phe  Thr  Phe  Ser  Asp  Tyr
                           20                       25                       30

Tyr  Met  Tyr  Trp  Val  Arg  Gln  Ala  Pro  Gly  Lys  Gly  Leu  Glu  Trp  Val
                           35                       40                       45

Ala  Tyr  Met  Ser  Asn  Val  Gly  Ala  Ile  Thr  Asp  Tyr  Pro  Asp  Thr  Val
                     50                        55                       60

Lys  Gly  Arg  Phe  Thr  Ile  Ser  Arg  Asp  Asn  Ala  Lys  Ser  Thr  Leu  Phe
            65                            70                       75                   80

Leu  Gln  Met  Asp  Ser  Leu  Arg  Pro  Glu  Asp  Thr  Gly  Val  Tyr  Phe  Cys
                           85                       90                       95

Ala  Arg  Gly  Thr  Arg  Asp  Gly  Ser  Trp  Phe  Ala  Tyr  Trp  Gly  Gln  Gly
                          100                      105                      110
```

Thr Pro Val Thr Val Ser Ser
115

(2) INFORMATION FOR SEQ ID NO:24:

(i) SEQUENCE CHARACTERISTICS:
      (A) LENGTH: 119 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:24:

Glu Val Gln Leu Val Glu Ser Gly Gly Val Val Gln Pro Gly Arg
1               5                   10                  15

Ser Leu Arg Leu Ser Cys Ser Ser Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Met Ser Asn Val Gly Ala Ile Thr Asp Tyr Pro Asp Thr Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Pro Glu Asp Thr Gly Val Tyr Phe Cys
                85                  90                  95

Ala Arg Gly Thr Arg Asp Gly Ser Trp Phe Ala Tyr Trp Gly Gln Gly
            100                 105                 110

Thr Pro Val Thr Val Ser Ser
            115

(2) INFORMATION FOR SEQ ID NO:25:

(i) SEQUENCE CHARACTERISTICS:
      (A) LENGTH: 112 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:25:

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Val His Ser
            20                  25                  30

Asn Gly Asn Thr Tyr Leu Glu Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Tyr Thr Phe Thr Ile
65                  70                  75                  80

Ser Ser Leu Gln Pro Glu Asp Ile Ala Thr Tyr Tyr Cys Phe Gln Gly
                85                  90                  95

Ser His Val Pro Phe Thr Phe Gly Gln Gly Thr Lys Leu Gln Ile Thr
            100                 105                 110

(2) INFORMATION FOR SEQ ID NO:26:

(i) SEQUENCE CHARACTERISTICS:
      (A) LENGTH: 357 base pairs
      (B) TYPE: nucleic acid (C) STRANDEDNESS: unknown
(D) TOPOLOGY: unknown (ii) MOLECULE TYPE: DNA (xi) SEQUENCE DESCRIPTION: SEQ ID NO:26:

| | | | | | |
|---|---|---|---|---|---|
| GAAGTGAAGC | TGGTGGAGTC | GGGGGGAGGC | TTAGTGCAGC | CTGGAGGGTC | CCTGAAACTC | 60 |
| TCCTGTGCAA | CCTCTGGATT | CACTTTCAGT | GACTATTACA | TGTATTGGGT | TCGCCAGACT | 120 |
| CCAGAGAAGA | GGCTGGAGTG | GGTCGCATAC | ATGAGTAATG | TTGGTGCTAT | CACCGATTAT | 180 |
| CCAGACACTG | TAAAGGGCCG | ATTCACCATC | TCCAGAGACA | ATGCCAAGAG | CACCCTGTAC | 240 |
| CTGCAAATGA | GCCGTCTGAG | GTCTGAGGAC | ACAGCCATGT | ATTACTGTGC | AAGAGGGACG | 300 |
| CGGGATGGTT | CCTGGTTTGC | TTACTGGGGC | CAAGGGACTC | TGGTCACTGT | CTCTGCA | 357 |

(2) INFORMATION FOR SEQ ID NO:27:

(i) SEQUENCE CHARACTERISTICS:
(A) LENGTH: 119 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:27:

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Met Ser Asn Val Gly Ala Ile Thr Asp Tyr Pro Asp Thr Val
    50                  55                  60

Lys Gly Arg Phe Thr Ile Ser Arg Asp Asn Ala Lys Ser Thr Leu Tyr
65                  70                  75                  80

Leu Gln Met Ser Arg Leu Arg Ser Glu Asp Thr Ala Met Tyr Tyr Cys
            85                  90                  95

Ala Arg Gly Thr Arg Asp Gly Ser Trp Phe Ala Tyr Trp Gly Gln Gly
                100                 105                 110

Thr Leu Val Thr Val Ser Ala
            115

(2) INFORMATION FOR SEQ ID NO:28:

(i) SEQUENCE CHARACTERISTICS:
(A) LENGTH: 336 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:28:

| | | | | | |
|---|---|---|---|---|---|
| GATGTTTTGA | TGACCCAAAC | TCCACTCTCC | CTGCCTGTCA | GTCTTGGAGA | TCAAGCCTCC | 60 |
| ATCTCTTGCA | GATCTAGTCA | GCGCATTGTA | CATAGTAATG | GAAACACCTA | TTTAGAATGG | 120 |
| TACCTGCAGA | AACCAGGCCA | GTCTCCAAAG | CTCCTGATCT | ACAAAGTTTC | CAACCGATTT | 180 |
| TCTGGGGTCC | CAGACAGGTT | CAGTGGCAGT | GGATCAGGGA | CAGATTTCAC | ACTCAAGATC | 240 |
| AGCAGAGTGG | AGGCTGAGGA | TCTGGGAGTT | TATTACTGCT | TTCAAGGTTC | ACATGTTCCA | 300 |
| TTCACGTTCG | GCTCGGGGAC | AAAGTTGGAA | ATAAAA | | | 336 |

(2) INFORMATION FOR SEQ ID NO:29:

(i) SEQUENCE CHARACTERISTICS:
    (A) LENGTH: 112 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:29:

```
Asp Val Leu Met Thr Gln Thr Pro Leu Ser Leu Pro Val Ser Leu Gly
  1               5                  10                  15
Asp Gln Ala Ser Ile Ser Cys Arg Ser Gln Arg Ile Val His Ser
             20                  25                  30
Asn Gly Asn Thr Tyr Leu Glu Trp Tyr Leu Gln Lys Pro Gly Gln Ser
             35                  40                  45
Pro Lys Leu Leu Ile Tyr Lys Val Ser Asn Arg Phe Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Phe Thr Phe Gly Ser Gly Thr Lys Leu Glu Ile Lys
            100                 105                 110
```

(2) INFORMATION FOR SEQ ID NO:30:

(i) SEQUENCE CHARACTERISTICS:
    (A) LENGTH: 357 base pairs
    (B) TYPE: nucleic acid
    (C) STRANDEDNESS: unknown
    (D) TOPOLOGY: unknown (ii) MOLECULE TYPE: DNA (xi) SEQUENCE DESCRIPTION: SEQ ID NO:30:

```
GAGGTCCAAC TGGTGGAGAG CGGTGGAGGT GTTGTGCAAC CTGGCCGGTC CCTGCGCCTG      60
TCCTGCTCCT CGTCTGGCTT CACTTTCAGT GACTATTACA TGTATTGGGT GAGACAGGCA     120
CCTGGAAAAG GTCTTGAGTG GGTTGCATAC ATGAGTAATG TTGGTGCTAT CACCGACTAT     180
CCAGACACTG TGAAGGGGAG ATTTACAATA TCGAGAGACA ACAGCAAGAA CACATTGTTC     240
CTGCAAATGG ACAGCCTGAG ACCCGAAGAC ACCGGGGTCT ATTTTTGTGC AAGAGGCACC     300
CGTGATGGCT CGTGGTTTGC TTACTGGGGC CAAGGGACCC CGGTCACCGT CTCCTCA       357
```

(2) INFORMATION FOR SEQ ID NO:31:

(i) SEQUENCE CHARACTERISTICS:
    (A) LENGTH: 119 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:31:

```
Glu Val Gln Leu Val Glu Ser Gly Gly Gly Val Val Gln Pro Gly Arg
  1               5                  10                  15
Ser Leu Arg Leu Ser Cys Ser Ser Gly Phe Thr Phe Ser Asp Tyr
             20                  25                  30
Tyr Met Tyr Trp Val Arg Gln Ala Pro Gly Lys Gly Leu Glu Trp Val
```

|  |  |  | 35 |  |  |  | 40 |  |  |  | 45 |  |  |
|---|---|---|---|---|---|---|---|---|---|---|---|---|---|
| Ala | Tyr | Met | Ser | Asn | Val | Gly | Ala | Ile | Thr | Asp | Tyr | Pro | Asp | Thr | Val |
|  | 50 |  |  |  | 55 |  |  |  |  | 60 |  |  |  |
| Lys | Gly | Arg | Phe | Thr | Ile | Ser | Arg | Asp | Asn | Ser | Lys | Asn | Thr | Leu | Phe |
| 65 |  |  |  | 70 |  |  |  |  | 75 |  |  |  |  | 80 |
| Leu | Gln | Met | Asp | Ser | Leu | Arg | Pro | Glu | Asp | Thr | Gly | Val | Tyr | Phe | Cys |
|  |  |  | 85 |  |  |  |  | 90 |  |  |  |  | 95 |  |
| Ala | Arg | Gly | Thr | Arg | Asp | Gly | Ser | Trp | Phe | Ala | Tyr | Trp | Gly | Gln | Gly |
|  |  |  | 100 |  |  |  |  | 105 |  |  |  |  | 110 |  |
| Thr | Pro | Val | Thr | Val | Ser | Ser |
|  |  |  | 115 |  |  |  |

( 2 ) INFORMATION FOR SEQ ID NO:32:

( i ) SEQUENCE CHARACTERISTICS:
        ( A ) LENGTH: 336 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:32:

| GACATCCAGA | TGACCCAGAG | CCCAAGCAGC | CTGAGCGCCA | GCGTGGGTGA | CAGAGTGACC | 60 |
| ATCACCTGTA | GATCTAGTCA | GCGCATTGTA | CATAGTAATG | GAAACACCTA | TTTAGAATGG | 120 |
| TACCAGCAGA | CGCCAGGTAA | GGCTCCAAAG | CTGCTGATCT | ACAAAGTTTC | CAACCGATTT | 180 |
| TCTGGTGTGC | CAAGCAGATT | CAGCGGTAGC | GGTAGCGGTA | CCGACTACAC | CTTCACCATC | 240 |
| AGCAGCCTCC | AGCCAGAGGA | CATCGCCACC | TACTACTGCT | TTCAAGGTTC | ACATGTTCCC | 300 |
| TTCACGTTCG | GCCAAGGGAC | CAAGCTGCAA | ATCACA |  |  | 336 |

( 2 ) INFORMATION FOR SEQ ID NO:33:

( i ) SEQUENCE CHARACTERISTICS:
        ( A ) LENGTH: 112 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:33:

| Asp | Ile | Gln | Met | Thr | Gln | Ser | Pro | Ser | Ser | Leu | Ser | Ala | Ser | Val | Gly |
| 1 |  |  |  | 5 |  |  |  |  | 10 |  |  |  |  | 15 |  |
| Asp | Arg | Val | Thr | Ile | Thr | Cys | Arg | Ser | Ser | Gln | Arg | Ile | Val | His | Ser |
|  |  |  | 20 |  |  |  |  | 25 |  |  |  |  | 30 |  |  |
| Asn | Gly | Asn | Thr | Tyr | Leu | Glu | Trp | Tyr | Gln | Gln | Thr | Pro | Gly | Lys | Ala |
|  |  | 35 |  |  |  |  | 40 |  |  |  |  | 45 |  |  |  |
| Pro | Lys | Leu | Leu | Ile | Tyr | Lys | Val | Ser | Asn | Arg | Phe | Ser | Gly | Val | Pro |
|  | 50 |  |  |  |  | 55 |  |  |  |  | 60 |  |  |  |  |
| Ser | Arg | Phe | Ser | Gly | Ser | Gly | Ser | Gly | Thr | Asp | Tyr | Thr | Phe | Thr | Ile |
| 65 |  |  |  |  | 70 |  |  |  |  | 75 |  |  |  |  | 80 |
| Ser | Ser | Leu | Gln | Pro | Glu | Asp | Ile | Ala | Thr | Tyr | Tyr | Cys | Phe | Gln | Gly |
|  |  |  |  | 85 |  |  |  |  | 90 |  |  |  |  | 95 |  |
| Ser | His | Val | Pro | Phe | Thr | Phe | Gly | Gln | Gly | Thr | Lys | Leu | Gln | Ile | Thr |
|  |  |  | 100 |  |  |  |  | 105 |  |  |  |  | 110 |  |  |

What is claimed is:

1. A method of detecting cancer cells which express the Lewis Y antigen in a human, said method comprising the steps of: administering a composition comprising a labeled humanized antibody to a test subject, wherein said humanized antibody comprises a humanized variable region having a heavy chain variable region selected from the group consisting of 3S193 HuVH (SEQ. ID. NO: 20), 3S193 HuVHT (SEQ. ID. NO: 21), 3S193 HuVHA (SEQ. ID. NO: 22), 3S193 HuVHAS (SEQ. ID. NO: 23), and 3S193 HuVHASY (SEQ. ID. NO: 24), and a light chain variable region selected from the group consisting of 3S 193 HuVK (SEQ. ID. NO: 25) and 3S193 HuVKF (SEQ. ID. NO: 33), whereby the labeled humanized antibody binds to changer cells expressing the Lewis Y antigen, and detecting the bound labeled humanized antibody.

2. The method according to claim 1, wherein the humanized antibody comprises the heavy chain variable region HuVH (SEQ. ID. NO: 20) and the light chain variable region HuVK (SEQ ID NO: 25).

3. The method according to claim 1, wherein the humanized antibody comprises the heavy chain variable region HuVHT (SEQ ID NO: 21) and the light chain variable region HuVKF (SEQ ID NO: 33).

4. The method according to claim 1, wherein the humanized antibody comprises the heavy chain variable region HuVHT (SEQ ID NO: 21) and the light chain variable region HuVK (SEQ ID NO: 25).

5. The method according to claim 1, wherein the humanized antibody comprises the heavy chain variable region HuVHA (SEQ ID NO: 22) and the light chain variable region HuVKF (SEQ ID NO: 33).

6. The method according to claim 1, wherein the humanized antibody comprises the heavy chain variable region HuVHAS (SEQ ID NO: 23) and the light chain variable region HuVKF (SEQ ID NO: 33).

7. The method according to claim 1, wherein the humanized antibody comprises the heavy chain variable region HuVHASY (SEQ ID NO: 24) and the light chain variable region HuVKF (SEQ ID NO: 33).

* * * * *

UNITED STATES PATENT AND TRADEMARK OFFICE
CERTIFICATE OF CORRECTION

PATENT NO.    : 5,874,060　　　　　　　　　　　　　　　　　　　　Page 1 of 1
DATED         : February 23, 1999
INVENTOR(S)   : Kathryn Lesley Armour, et al It is certified that error appears in the above-identified patent and that said Letters Patent is hereby corrected as shown below:

Column 6,
Line 67, change "reference" to -- reference. --.

Column 8,
Line 37, change "550°" to -- 55° --.
Line 38, change "720°" to -- 72° -- on two separate occasions.

Column 9,
Line 62, change "500° C" to -- 50° C --.
Line 62, change "750° C" to -- 75° C --.

Column 14,
Line 26, change "7G" to -- 76 --.

Column 15,
Line 66, change "rosetting" to -- lysis --.

Column 16,
Line 6, change "(+/-)" to -- 50° --.

Column 37,
Line 14, change "changer" to -- cancer --.

Signed and Sealed this

Eleventh Day of September, 2001

Attest:

*Nicholas P. Godici*

NICHOLAS P. GODICI
*Attesting Officer*　　　*Acting Director of the United States Patent and Trademark Office*